United States Patent
Smedegaard et al.

(10) Patent No.: US 6,544,238 B1
(45) Date of Patent: Apr. 8, 2003

(54) INJECTION NEEDLE

(75) Inventors: Jørgen K Smedegaard, Frederiksberg (DK); Kim Steengaard, Birkerød (DK); Henning Munk Ejlersen, Vedbæk (DK)

(73) Assignee: Novo Nordisk A/S, Bagsvaerd (DK)

( * ) Notice: Subject to any disclaimer, the term of this patent is extended or adjusted under 35 U.S.C. 154(b) by 548 days.

(21) Appl. No.: 09/043,950

(22) PCT Filed: Dec. 17, 1996

(86) PCT No.: PCT/DK96/00537

§ 371 (c)(1),
(2), (4) Date: Mar. 27, 1998

(87) PCT Pub. No.: WO97/23253

PCT Pub. Date: Jul. 3, 1997

(30) Foreign Application Priority Data

Dec. 22, 1995 (DK) ............................................. 1460/95
Apr. 24, 1996 (DK) ............................................. 0492/96

(51) Int. Cl.⁷ ............................ A61M 5/00; A61M 5/32
(52) U.S. Cl. ...................................... 604/272; 604/117
(58) Field of Search ................................. 604/115, 117, 604/239, 272, 274, 48, 264

(56) References Cited

U.S. PATENT DOCUMENTS

| | | | | |
|---|---|---|---|---|
| 4,235,234 A | * | 11/1980 | Whitney et al. ............ | 128/216 |
| 5,015,235 A | * | 5/1991 | Crossman .................... | 604/117 |
| 5,462,535 A | * | 10/1995 | Bonnichsen et al. ........ | 604/272 |
| 5,599,309 A | * | 2/1997 | Marshall et al. ............ | 604/136 |
| 5,674,205 A | * | 10/1997 | Pasricha et al. ............. | 604/232 |
| 5,944,700 A | * | 8/1999 | Nguyen et al. .............. | 604/263 |

FOREIGN PATENT DOCUMENTS

| | | |
|---|---|---|
| JP | 27-3595 | 11/1950 |
| JP | 61-22984 | 6/1986 |
| JP | UM 3020799 | 11/1995 |

OTHER PUBLICATIONS

Rufenacht & Latchaw, Table 5 "Conversion Chart for MM, Inch, French and Gauge", p. 256.*

* cited by examiner

Primary Examiner—Angela D. Sykes
Assistant Examiner—Patricia Bianco
(74) Attorney, Agent, or Firm—Skadden, Arps, Slate Meagher & Flom LLP

(57) ABSTRACT

A needle assembly comprises an injection needle and a needle hub, mountable on a syringe, for securing the injection needle. The needle has an injection part extending axially from the hub and terminating in a skin piercing obliquely cut end. The length of the injection part is between 4 and 6 mm, thereby facilitating a proper subcutaneous injection. Also, preferably either (a) the outer diameter of the needle is smaller than 0.320 mm and the bore diameter is larger than 0.165 mm, or (b) the outer diameter is smaller than 0.298 mm and the bore diameter is larger than 0.133 mm. Also, preferably the hub includes an axially extending protrusion, from which the injection part extends, to facilitate insertion of the injection part into the skin of a user at an oblique angle.

3 Claims, 1 Drawing Sheet

INJECTION NEEDLE

BACKGROUND OF THE INVENTION

The invention relates to injection needles mounted in needle hubs, the needles having an injection part with a skin piercing obliquely cut end and being fastened in the needle hub for mounting on a syringe.

Such needles are often shaped as double pointed needles in which each needle, in addition to a skin piercing point, has at the other end of the needle a point which pierces a rubber membrane which closes an ampoule containing the liquid to be injected.

Needles of the above kind are used for injection of liquids, e.g. insulin, which have to be injected subcoutaneously. i.e. in the subcutis lying between the cutis and a muscle membrane which cover the underlying muscles. If insulin is injected into the muscle it will be absorbed in the body too quickly and an unwanted drop in the blood sugar level may be the result. On the other hand insulin injected in the cutis will not be absorbed at all or in an unpredictable way.

To be sure that intramuscular injection is avoided an injection technique may be used by which the skin is gripped by one hand between the thumb and the side of the index finger so that a fold of the skin is formed and thereafter the needle insertion and the injection are performed with the injection device held in the other hand. The technique described makes the injection a two hand operation, and even a third hand could be useful for drawing and keeping away clothes normally covering the injection zone.

It is an object of the invention to provide a needle suited for use by subcoutaneous injections which needle may mainly be inserted without making it necessary to form a fold of the skin and by which the injection consequently occupies only one hand. Allthough the injection of insulin is described as an example, the needle is useful for all kinds of subcoutaneus injections, e.g. for injecton of growth hormone.

EP 279 583 mentions the provision of needles the injection part of which has an overall length of 8–12 mm. This length will seen in relation to the often used 16 mm needles reduce the risk for performing intramuscular injections, but by slim males the sum of the thicknesses of the cutis and the subcutis may even be smaller than 8 mm and the risk for intramuscular injection will still be unacceptable.

From EP 279 583 it is known to reduce the effective length of a 12.5 mm long needle by mounting on the needle hub a skirt surrounding the needle coaxially in a distance from said needle. The skirt only leaves a minor length of the needle free for injection. Skirts of different lengths may be used to leave 4 or 8 mm of the needle free for penetration of the skin. The effective length of the needle is only well defined by insertion perpendicular to the skin whereas the effective length is further reduced in a not well defined way if the needle is inserted at an oblique angle.

BRIEF SUMMARY OF THE INVENTION

Needles having lengths between 3 mm and 4 mm have been discussed but being that short a needle will hardly be able to penetrate the cutis, especially not when the needle is inserted at an oblique angle.

The risk of making intramuscular injections or injections in cutis is heavily reduced when a needle is used by which according to the invention the overall length of the injection part of the needle extending from its fastening in the needle hub to its skin piercing end lies in the interval 4–6 mm.

The shorter overall length of the injection part of the needle counted from its support in the hub to the skin piercing point enables use of thin and thin walled needles with reduced risk for cracking. This reduced risk is not obtained by needles the effective length of which are reduced by surrounding a part of the needle with a sleeve which does not support the needle.

As it is possible to administer insulin through needles as thin as G30, administration will also be possible through a thin walled needle having a bore larger than 0.133 mm which corresponds to the smallest bore of a G30 needle. If the outer diameter is set as the largest diameter allowed for a G30 needle, thin walls will allow a larger bore than known from a normal G30 needle.

According to an embodiment of the invention the outer diameter of the needle and the diameter of the bore of the needle may comply with one of the following conditions:

a) the outer diameter is smaller than 0.320 mm and the diameter of the bore is larger than 0.165 mm, or b) the outer diameter is smaller than 0.298 mm and the diameter of the bore is larger than 0.133 mm.

In the following the invention is described in more details with reference to the drawing.

DETAILED DESCRIPTION OF THE INVENTION

Figure 1:
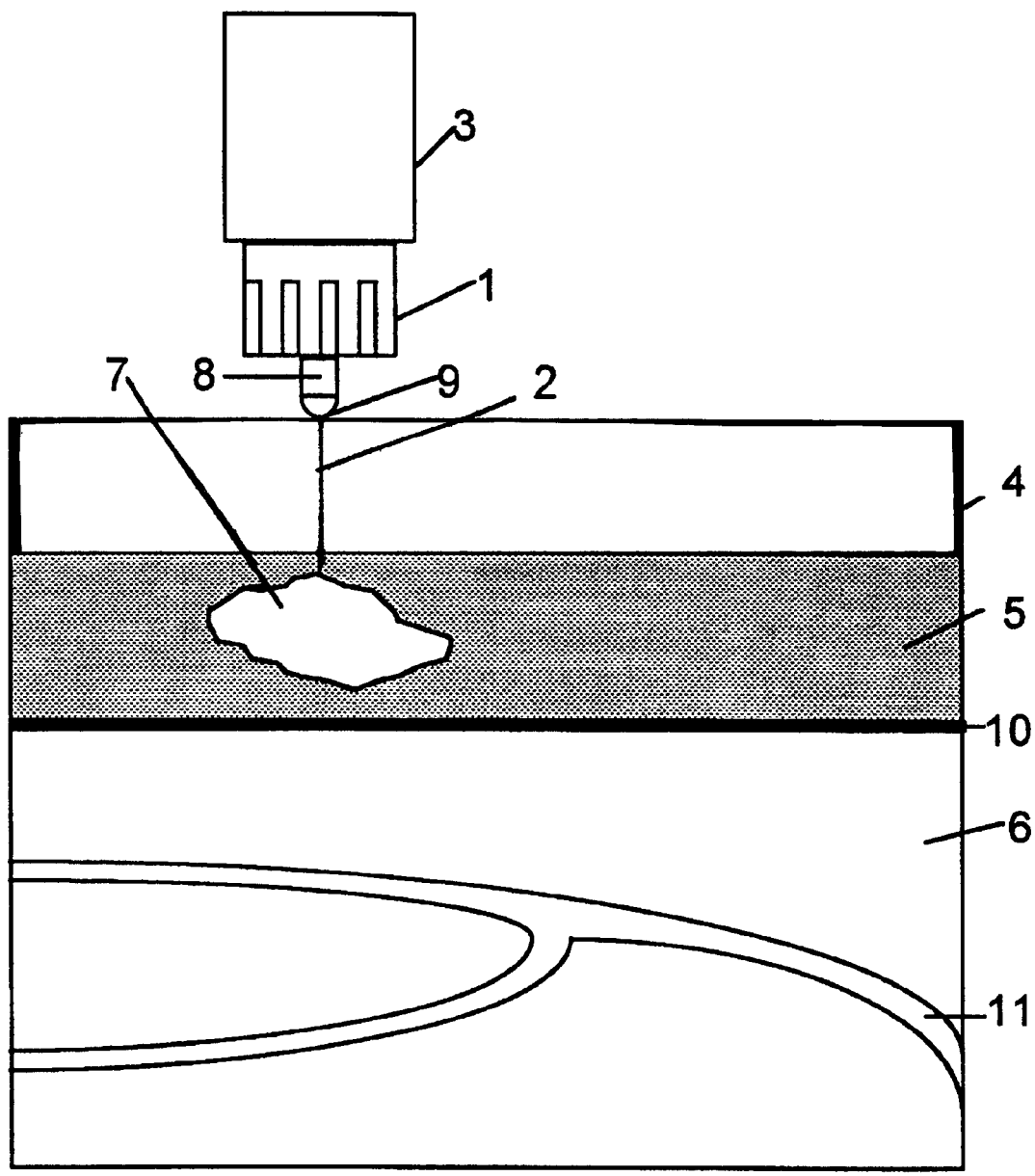
FIG. 1 schematically shows a needle inserted into a zone of skin with an underlying muscle.

In FIG. 1 a needle hub 1 carrying an injection needle 2 is mounted on a syringe 3. The injection needle 2 is inserted through a cutis layer 4 into a subcutis layer 5 which is by a muscle membrane 10 separated from a muscle tissue 6 with blood vessels 11. An injected not yet absorbed amount of liquid in the subcutis is designated by the number 7.

Where the needle 2 is fastened in the hub 1 this hub has a protrusion 8 which is terminated by a dome 9. By this construction the injection part of the needle may be obliquely inserted in its full length whereas a full insertion is only possible by insertion of the needle perpendicularly to the skin if the injection part of the needle extends directly from the end surface of the hub.

By a number of measurements it has been found that the thickness of the cutis and subcutis lies in the intervals described in the following table. The mean values may be seen as the values valid for the preferred injection zones.

TABLE OF SKIN THICKNESS VALUES

|  | Females | | | Males | | |
| --- | --- | --- | --- | --- | --- | --- |
|  | min | max | mean | min | max | mean |
| cutis | 1.1 | 3.6 | 1.7 | 1.2 | 4.1 | 2.3 |
| subcutis | 4.5 | 30.8 | 12.1 | 2.3 | 26.9 | 7.2 |
| sum | 5.6 | 34.4 | 13.8 | 3.5 | 31.0 | 9.5 |

Recognizing that the emission of liquid from the needle due to the oblique cut of the end of this needle takes place in a range in a distance from the point of the needle, e.g. in a G30 needle in the range 0.4–1.2 mm from the point of the needle, it is seen that by women even an injection with a 6 mm needle perpendicular to the skin in a zone where the skin thickness is minimum, will not reach the muscle whereas an injection with a 4 mm needle is possible when the zones with the thickest cutis is avoided.

Using a 6 mm needle men should avoid injection in the zones where the skin thickness is minimum and such zone are actually not attractive for injections. A 4 mm needle cannot be used in zones where the cutis has its maximum thickness, but these zones also lie beyond the zones normally preferred for injection which are the abdomen and the thighs.

If the needle is inserted under an oblique angle the skin may be looked upon as having a thickness which is the thickness in the above table divided by the sine of the angle between the needle aid the skin surface. By an angle of 45° this corresponds to a multiplication by 1.4.

It is seen that women can use a 6 mm needle universally for injections with the needle perpendicular to the skin surface or forming an angle with this surface, whereas a 4 mm needle may not be used without keeping the needle perpendicular to the skin surface when injections are made in zones where the cutis has its maximum thickness.

Neither in the zones where the skin has it minimum thickness nor the zones where the skin has its maximum thickness men should use a 6 mm needle even when it is inserted under an oblique angle in the first mentioned zones the 6 mm needle may reach the muscle and in the last mentioned zones the needle may not reach through the cutis. In the zones where the skin has its minimum thickness a 4 mm needle may be used when it is inserted under an oblique angle to the skin.

Whereas the zones wherein the skin has its minimum thickness are mainly not attractive as injection zones, the condition in these zones corresponds to the conditions met in the preferred injection zones by skinny people, especially skinny children.

However in the preferred injection zones represented by the mean values for the thicknesses of the cutis and subcutis a 4 mm needle as well as a 6 mm needle may be used perpendicularly to the skin surface or forming an oblique angle with that surface leaving an acceptable margin for variations around the mean value of the thickness of the skin layers.

What is claimed is:

1. A needle assembly comprising an injection needle and a needle hub mountable on a syringe, wherein said hub includes a center portion securing said injection needle in said hub, wherein said needle has an injection part projecting axially from said center portion and terminating in a skin piercing obliquely cut end, where the length of the injection part lies in the interval 4–6 mm.

2. An injection needle according to claim 1, wherein the needle has an outer diameter and a bore diameter which comply with one of the following conditions:

a) the outer diameter is smaller than 0.320 mm and the bore diameter is larger than 0.165 mm, or b) the outer diameter is smaller than 0.298 mm and the bore diameter is larger than 0.133 mm.

3. A needle assembly according to claim 1, wherein said center portion comprises an axially extending protrusion, from which said injection part extends, to facilitate insertion of the injection part into the skin of a user at an oblique angle.

\* \* \* \* \*